US010065352B2

(12) United States Patent
McGrath et al.

(10) Patent No.: US 10,065,352 B2
(45) Date of Patent: Sep. 4, 2018

(54) SYSTEM AND METHOD FOR MANDREL-LESS ELECTROSPINNING

(71) Applicant: Neograft Technologies, Inc., Taunton, MA (US)

(72) Inventors: Jon McGrath, Duxbury, MA (US); Lorenzo Soletti, Pittsburgh, PA (US); Mohammed S. El-Kurdi, Mansfield, MA (US); William R. Wagner, Wexford, PA (US); J. Christopher Flaherty, Aburndale, FL (US)

(73) Assignees: Neograft Technologies, Inc., Taunton, MA (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/499,242

(22) Filed: Apr. 27, 2017

(65) Prior Publication Data
US 2017/0326772 A1   Nov. 16, 2017

Related U.S. Application Data

(63) Continuation of application No. 13/997,933, filed as application No. PCT/US2011/066905 on Dec. 22, 2011, now Pat. No. 9,656,417.
(Continued)

(51) Int. Cl.
*B29C 47/00*   (2006.01)
*D01D 5/00*   (2006.01)
(Continued)

(52) U.S. Cl.
CPC .......... *B29C 47/0076* (2013.01); *A61F 2/06* (2013.01); *A61F 2/062* (2013.01); *A61L 27/14* (2013.01);
(Continued)

(58) Field of Classification Search
CPC ...... B29C 47/0076; A61L 27/28; A61L 27/50; A61L 27/14; A61L 2/062; D04H 1/728; A61F 2/06; A61F 2240/001
(Continued)

(56) References Cited

U.S. PATENT DOCUMENTS 3,376,180 A   4/1968   Larson et al.
4,950,239 A   8/1990   Gahara et al.
(Continued)

FOREIGN PATENT DOCUMENTS

EP   0095940 A2   12/1983
KR   100595487 B1   7/2006
(Continued)

OTHER PUBLICATIONS

Ayres, et al. Modulation of anisotropy in electrospun tissue-engineering scaffolds: Analysis of fiber alignment by the fast Fourier transform. Biomaterials 27 (2006) 5524-5534.
(Continued)

*Primary Examiner* — Nahida Sultana
(74) *Attorney, Agent, or Firm* — Wilson Sonsini Goodrich & Rosati

(57) ABSTRACT

A system for electrospinning a fiber matrix on a tubular member includes at least one nozzle, a tubular member in a spaced relationship to the at least one nozzle, and a fluid source for pressurizing a lumen of the tubular member. An electrical potential is applied between the at least one nozzle and either the tubular member or fluid from the fluid source. The electrical potential draws at least one fiber from the at least one nozzle to the tubular member.

16 Claims, 5 Drawing Sheets

Related U.S. Application Data

(60) Provisional application No. 61/427,993, filed on Dec. 29, 2010.

(51) Int. Cl.

| | | |
|---|---|---|
| *A61F 2/06* | (2013.01) | |
| *A61L 27/14* | (2006.01) | |
| *A61L 27/50* | (2006.01) | |
| *D04H 1/728* | (2012.01) | |
| *A61L 27/38* | (2006.01) | |

(52) U.S. Cl.
CPC ............... *A61L 27/38* (2013.01); *A61L 27/50* (2013.01); *D01D 5/0076* (2013.01); *D04H 1/728* (2013.01); *A61F 2240/001* (2013.01)

(58) Field of Classification Search
USPC ........ 264/465, 484, 510, 512, 514; 425/113, 425/174, 382.2
See application file for complete search history.

(56) References Cited

U.S. PATENT DOCUMENTS

| | | | |
|---|---|---|---|
| 5,127,783 A * | 7/1992 | Moghe | B29C 70/222 156/172 |
| 5,647,848 A | 7/1997 | Jorgensen | |
| 5,853,408 A | 12/1998 | Muni | |
| 6,056,993 A | 5/2000 | Leidner et al. | |
| 6,189,286 B1 * | 2/2001 | Seible | E04C 3/20 52/834 |
| 6,891,077 B2 | 5/2005 | Rothwell et al. | |
| 7,641,844 B2 | 1/2010 | Melsheimer | |
| 7,759,099 B2 | 7/2010 | Wolf et al. | |
| 7,759,120 B2 | 7/2010 | Wolf et al. | |
| 7,998,188 B2 | 8/2011 | Zilla et al. | |
| 8,057,537 B2 | 11/2011 | Zilla et al. | |
| 8,076,529 B2 | 12/2011 | Ehrenreich et al. | |
| 8,172,746 B2 | 5/2012 | Zilla et al. | |
| 8,353,814 B2 | 1/2013 | Villafana et al. | |
| 8,889,573 B2 | 11/2014 | Kamisasa | |
| 9,656,417 B2 | 5/2017 | McGrath et al. | |
| 2002/0042128 A1 | 4/2002 | Bowlin et al. | |
| 2003/0093107 A1 | 5/2003 | Parsonage et al. | |
| 2004/0094873 A1 | 5/2004 | Dubson et al. | |
| 2004/0146546 A1 | 7/2004 | Gravett et al. | |
| 2005/0020870 A1 * | 1/2005 | Suzuki | A61M 1/1037 600/16 |
| 2005/0203636 A1 | 9/2005 | McFetridge | |
| 2005/0251107 A1 | 11/2005 | Olson | |
| 2006/0234051 A1 * | 10/2006 | Zhang | D01D 5/098 428/373 |
| 2006/0240061 A1 | 10/2006 | Atala et al. | |
| 2007/0003653 A1 | 1/2007 | Ahle et al. | |
| 2007/0207179 A1 | 9/2007 | Andersen et al. | |
| 2007/0255206 A1 | 11/2007 | Reneker et al. | |
| 2007/0269481 A1 | 11/2007 | Li et al. | |
| 2007/0293932 A1 | 12/2007 | Zilla et al. | |
| 2008/0157444 A1 | 7/2008 | Melsheimer | |
| 2008/0188924 A1 | 8/2008 | Prabhu | |
| 2008/0208323 A1 | 8/2008 | El-Kurdi et al. | |
| 2010/0081992 A1 | 4/2010 | Ehrenreich et al. | |
| 2010/0092687 A1 * | 4/2010 | Sumida | D01D 5/0061 427/472 |
| 2010/0160718 A1 | 6/2010 | Villafana et al. | |
| 2010/0168836 A1 * | 7/2010 | Kassab | A61B 5/053 623/1.11 |
| 2010/0233115 A1 | 9/2010 | Patel et al. | |
| 2011/0135806 A1 | 6/2011 | Grewe et al. | |
| 2011/0156319 A1 * | 6/2011 | Kurokawa | D01D 5/0061 264/466 |
| 2011/0198327 A1 | 8/2011 | Prabhu | |
| 2011/0213454 A1 | 9/2011 | Zilla et al. | |
| 2012/0116495 A1 | 5/2012 | Zilla et al. | |
| 2013/0337101 A1 | 12/2013 | McGrath et al. | |
| 2014/0079758 A1 | 3/2014 | Hall et al. | |
| 2014/0081414 A1 | 3/2014 | Hall et al. | |
| 2014/0141152 A1 | 5/2014 | Sostek et al. | |
| 2014/0288632 A1 * | 9/2014 | Soletti | A61F 2/06 623/1.13 |
| 2014/0315020 A1 | 10/2014 | Sun et al. | |
| 2014/0353882 A1 | 12/2014 | Joo et al. | |
| 2014/0357144 A1 | 12/2014 | Joseph et al. | |
| 2014/0379072 A1 | 12/2014 | Barbarash et al. | |
| 2015/0283473 A1 * | 10/2015 | Frazier | A63H 27/10 141/96 |
| 2015/0336318 A1 | 11/2015 | Porter et al. | |
| 2016/0287374 A1 * | 10/2016 | Soletti | A61L 27/34 |
| 2017/0312100 A1 * | 11/2017 | Soletti | A61F 2/82 |

FOREIGN PATENT DOCUMENTS

| | | |
|---|---|---|
| WO | WO-02070238 A1 | 9/2002 |
| WO | WO-2010042721 A1 | 4/2010 |

OTHER PUBLICATIONS

Ben-Gal, et al. Expandable external support device to improve saphenous vein graft patency after cabg. J Cardiothorac Surg 2013;8:122.

Castronuovo, J. The sequence of gene expression in cultured human saphenous vein after injury. (2002) J. Vasc. Surg. 35, 146-151.

Chakrabarty, S. Fibrin solubilizing properties of certain anionic and cationic detergents. Thrombosis research 55.4 (1989): 511-519.

Courtney, et al. Design and anlysis of tissue engineering scaffolds that mimic soft tissue mechanical anisotropy. Biomaterials. 2006, 27: 3631-3638.

Deitzel, et al. Controlled deposition of electrospun poly(ethylene oxide) fibers. Polymer. 2001, 42: 8163-8170.

Deitzel, et al. The effect of processing variable on the morphology of electrospun nanofibers and textiles. Polymer 42 (2001): 261-272.

Fingerle. Intimal lesion formation in rat carotid arteries after endothelial denudation in absence of medial injury. (1990) Arteriosclerosis, 10, 1082-1087.

Grote, et al. Mechanical stretch enhances mRNA expression and proenzyme release of matrix metalloproteinase-2 (MMP-2) via nad(p)h oxidase-derived reactive oxygen species. Circulation Research. 2003;92(11): 80-6.

Hermans, et al. Fibrin: structure and interactions. Seminars in thrombosis and hemostasis. vol. 8. No. 1. 1982.

International search report and written opinion dated Sep. 26, 2012 for PCT Application No. US2011/066905.

International search report and written opinion dated Oct. 12, 2014 for EP Application No. 11853662.2.

Izzat, et al. Influence of External Stent Size on Early Medial and Neointimal Thickening in a Pig Model of Saphenous Vein Bypass Crafting, Circulation, 94(7):1741-1745, 1996.

Janowski-Bell, et al. Histology of Blood Vessels—www2.victoriacollege.edu/dept/bio/Belltutorials/Histology%20Tutorial/Blood%20Vessels/Histology_of_ Blood_Vessels.html.

Jeremy, et al. A Bioabsorbable (Polyglactin), Nonrestrictive, External Sheath Inhibits Porcine Saphenous Vein Graft Thickening, Journal of Thoracic and Cardiovascular Surgery, 127(6):1766-1772, Jun. 2004.

Kohler, et al. The Effect of Rigid External Support on Vein Graft Adaptation to the Arterial Circulation, J.. Vasc. Surg., 9(2):277-285, 1989.

Levorson, et al. Fabrication and characterization of multiscale electrospun scaffolds for cartilage regeneration. Biomed Mater 2013;8:014103. doi:10.1088/1748-6041/8/1/014103.

Linder, V. Mouse model of arterial injury. (1993) Circ. Res., 73, 792-796.

Manchio, J. Disruption of graft endothelium correlates with early failure after off-pump coronary artery bypass surgery. (2005) Ann. Thor. Surg. 79, 1991-1998.

McManus, et al. Electrospun fibrinogen: feasibility as a tissue engineering scaffold in a rat cell culture model. Journal of Biomedical Materials Research Part A 81.2 (2007): 299-309.

(56) References Cited

OTHER PUBLICATIONS

McManus, et al. Mechanical properties of electrospun fibrinogen structures. Acta Biomaterialia 2.1 (2006): 19-28.

Mehta, et al. External Stenting Reduces Long-term Medial and Neointimal Thickening and Platelet Derived Growth Factor Expression in a Pig Model of Arteriovenous Bypass Grafting, Nature Medicine, 4(2):235-239, Feb. 1998.

Morton, et al. Electrospun fibrin nanofibers for the use in tissue engineering. Modification of fibrin to improve applications in regenerative medicine (2010): 81.

Mosesson, M. W. Fibrinogen and fibrin structure and functions. Journal of Thrombosis and Haemostasis 3.8 (2005): 1894-1904.

Notice of Allowance dated Jan. 18, 2017 for U.S. Appl. No. 13/997,933.

Office action dated Mar. 11, 2015 for U.S. Appl. No. 13/997,933.

Office Action dated Jul. 11, 2016 for U.S. Appl. No. 13/997,933.

Office action dated Jul. 17, 2014 for U.S. Appl. No. 13/997,933.

Office action dated Oct. 2, 2015 for U.S. Appl. No. 13/997,933.

Parsonnet, et al. New stent for support of veins in arterial grafts. Arch Surg. 1963;87: 696-702.

Perumcherry, et al. A Novel Method for the Fabrication of Fibrin-Based Electrospun Nanofibrous Scaffold for Tissue-Engineering Applications*. Tissue Engineering Part C: Methods 17.11 (2011): 1121-1130.

Ramos, et al. Histologic fate and endothelial changes of distended and nondistended vein grafts. Ann Surg. 1976;183(3): 205-28.

Reneker, et al. Electrospinning of Nanofibers from Polymer Solutions and Melts. Adv Appl Mech 2007;41. doi:10.1016/S0065-2156(07)41002-X.

Sell, et al. Cross-linking methods of electrospun fibrinogen scaffolds for tissue engineering applications. Biomedical Materials 3.4 (2008): 045001.

Sepehipour, A. Does a 'no-touch' technique result in better vein patency? (2011) Interact Cardiovasc Thorac Surg., 13, 626-630.

Sreerekha, et al. Fabrication of fibrin based electrospun multiscale composite scaffold for tissue engineering applications. Journal of biomedical nanotechnology 9.5 (2013): 790-800.

Stankus, et al. Fabrication of biodegradable elastomeric scaffolds with sub-micron morphologies. J Biomed Mater Res A. 2004;70(4): 603-14.

Stitzel, et al. Controlled fabrication of a biological vascular substitute. Biomaterials. 2006, 27: 1088-1094.

Stooker, et al. Perivenous Application of Fibrin Glue Reduces Early Injury to the Human Saphenous Vein Graft Wall in an Ex Vivo Model, European Journal of Cardio-thoracic Surgery, 21(2):212-217, 2002.

Traver, et al. New Generation Tissue Sealants and Hemostatic Agents: Innovative Urologic Applications. Reviews in Urology. 2006, 8: 104-111.

Vijayan, et al. Long-term Reduction of Medial and Intimal Thickening in Porcine Saphenous Vein Grafts with a Polyglactin Biodegradable External Sheath, Journal Vascular Surgery, 40(5):1011-1019, 2004.

Wan, et al. Differential, time-dependent effects of perivenous application of fibrin glue on medial thickening in porcine saphenous vein grafts. European Journal of Cardio-thoracic Surgery, 29, (2006): 742-747.

Weisel, et al. Computer modeling of fibrin polymerization kinetics correlated with electron microscope and turbidity observations: clot structure and assembly are kinetically controlled. Biophysical journal 63.1 (1992): 111.

Weisel, et al. Mechanisms of fibrin polymerization and clinical implications. Blood 121.10 (2013): 1712-1719.

Wnek, et al. Electrospinning of nanofiber fibrinogen structures. Nano Letters 3.2 (2003): 213-216.

Xu, et al. Electrospun Nanofiber Fabrication as Synthetic Extracellular Matrix and Its Potential for Vascular Tissue Engineering. Tissue Engineering, vol. 10, No. 7/8, 2004.

Yu, et al. Electrospinning, Encyclopedia of Polymer Science & Technology (2008) 1-20.

Zilla, et al. Constrictive external nitinol meshes inhibit vein graft intimal hyperplasia in nonhuman primates. The Journal of Thoracic and Cardiovascular Surgery 2008;136:717-725.

Zilla, et al. Utilization of shape memory in external vein-graft meshes allows extreme diameter constriction for suppressing intimal hyperplasia: A non-human primate study. J Vasc Surg 2009;49:1532-42.

* cited by examiner

SYSTEM AND METHOD FOR MANDREL-LESS ELECTROSPINNING

CROSS-REFERENCE TO RELATED APPLICATION

This application is a continuation of U.S. application Ser. No. 13/997,933, filed Aug. 8, 2013, which is a National Phase of International Application No. PCT/US2011/066905, filed Dec. 22, 2011, which claims benefit of priority to U.S. Provisional Application No. 61/427,993, filed Dec. 29, 2010, each of which are incorporated by reference herein in their entirety.

FIELD OF THE INVENTION

The invention relates generally to systems and methods for mandrel-less electrospinning, and more particularly, to systems and methods for mandrel-less electrospinning a fiber matrix on a tubular member, such as, for example, a vein or artificial graft.

BACKGROUND OF THE INVENTION

Coronary artery disease, leading to myocardial infarction and ischemia, is a leading cause of morbidity and mortality worldwide. Conventional treatment alternatives consist of percutaneous transluminal angioplasty, stenting, and coronary artery bypass grafting ("CABG"). CABG can be carried out using either arterial or venous conduits and is an effective and widely used treatment to combat coronary arterial stenosis, with nearly 500,000 procedures being performed annually. In addition, there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia ("IH"), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts ("AVGs") remains a major problem: 12% to 27% of AVGs become occluded in the first year with a subsequent annual occlusive rate of 2% to 4%. Patients with failed arterial vein grafts (AVGs) can die or require re-operation.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells ("SMCs") and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

SUMMARY

For the above and other reasons, a need has been identified for devices and methods that can provide enhanced AVGs and other graft devices for mammalian patients. Desirably, the devices will improve long term patency and minimize surgical and device complications. Developing a reliable means to prevent the early events of the IH process and other luminal narrowing responses can contribute to improvements in the outcome of arterial bypass and other graft procedures. Therefore, systems and methods are provided for electrospinning a fiber matrix on a tubular member. For example, a tubular member can be wrapped with the fiber matrix. The tubular member can be, for example, harvested from a human being or animal, such as, a vein, artery, urethra, intestine, esophagus, trachea, bronchi, ureter, duct, or fallopian tube. The tubular member can be, for example, an artificial graft, compatible for use within the body of a patient. The tubular member is wrapped with a covering such as a fiber matrix, typically with a durable or biodegradable (also referred to as bioerodible or bioresorbable) polymer about a circumference of the tubular member.

The fiber matrix can be deposited on the tubular member by electrospinning. Typically, electrospinning involves insertion of a mandrel into the tubular member to support or hold open the tubular member while also providing a charged surface for creation of an electrical potential. The mandrel may also be used to transmit motion to the tubular member, such as translational or rotational motion. The mandrel usually is a mechanical device and oftentimes it is rigid. For example, the mandrel can be a cylindrical rod. A rod-type mandrel can be difficult to insert and/or remove and can damage the tubular member, such as a vein, directly. In addition, prior types of mandrels do not provide for any type of pressure control along the length of the tubular member. Moreover, prior types of mandrels do not easily adapt to different lengths or sizes of tubular members as multiple mandrels are required to accommodate different lengths and sizes of tubular members. Therefore, the system and method for electrospinning a fiber matrix onto a tubular member of the present invention can use a fluid source to provide a fluid mandrel. An advantage of utilizing a fluid mandrel is the provision of a less forceful contact between the tubular member and the mandrel than provided by a mechanical type of mandrel. In addition, a fluid mandrel allows for pressure adjustment across the length of the tubular member allowing for a better match between the mandrel and the tubular member than a mechanical type of mandrel. In addition, a fluid mandrel can allow drugs or other agents to be delivered to and/or embedded in the vein itself, providing a localized agent delivery method.

In one aspect, features a system for electrospinning a fiber matrix on a tubular member. The system includes at least one nozzle and a tubular member in a spaced relationship to the at least one nozzle. The system also includes a fluid source for pressurizing a lumen of the tubular member. An electrical potential is applied between the at least one nozzle and either the tubular member or fluid from the fluid source. The electrical potential draws at least one fiber from the at least one nozzle to the tubular member.

In another aspect, features a method for depositing a fiber matrix on a tubular member. The method includes providing a tubular member, providing a fluid source, for example an electrically conductive or dielectric fluid source, pressurizing a lumen of the tubular member with fluid from the fluid source, charging the tubular member and/or the fluid, and electrospinning a fiber matrix on the tubular member.

In another aspect, features a method for depositing a fiber matrix on a tubular member. A tubular member is inserted into an apparatus for applying an electrospun fiber matrix. A first portion of an electrospun fiber matrix is applied. A pressure is applied to the inside of the tubular member, and the tubular member elongates to a desired pressurized length. The tubular member is secured at a length different than its starting length, and another portion of the electrospun fiber matrix is applied.

In yet another aspect, features a method for depositing a fiber matrix on a tubular member. The tubular member is inserted into an apparatus for applying an electrospun fiber matrix. A pressure is applied to the inside of the tubular member, and the tubular member is allowed to elongate. The tubular member is secured at a length different than its starting length. Pressure is reduced within the tubular member and the tubular member is allowed to reduce in diameter while approximately maintaining the pressurized length. A fiber matrix is applied around the tubular member.

The systems and methods described herein can include one or more of the following described features.

In some embodiments, the pressure applied to the inside of the tubular member is approximately the same as arterial pressure, such as the patient's arterial pressure. The pressure applied to the inside of the tubular member can be approximately the same as venous pressure, such as the patient's venous pressure. The pressure applied to the inside of the tubular member can be lower than the arterial pressure. The luminal pressure applied within the tubular member can be negative relative to the outside of the tubular member.

In some embodiments, fluid from the fluid source, when used to pressurize the lumen of the tubular member, forms a fluid mandrel within the tubular member. The fluid source can pressurize the lumen of the tubular member at a pressure of approximately 20 mmHg. In some embodiments, the fluid source pressurizes the lumen of the tubular member at a pressure between about −30 mmHg and about 100 mmHg. The fluid source can pressurize the lumen of the tubular member at an approximate pressure selected from the group consisting of: 5 mmHg, 10 mmHg, 15 mmHg, 20 mmHg, 25 mmHg, 30 mmHg, 35 mmHg, and 40 mmHg. In some embodiments, the fluid source pressurizes the lumen of the tubular member with a varying pressure. The varying pressure can approximate an arterial pressure. The varying pressure can be less than an arterial pressure. The varying pressure can be between a venous pressure and an arterial pressure.

The system (and/or methods) can also include a first plug inserted at a first end of the tubular member and a second plug inserted at a second end of the tubular member to create a system for providing a fluid mandrel. In some embodiments, at least one of the first or second plugs rotate. The first and second plugs can be disposable. At least one of the first and second plugs can include a flow valve. In some embodiments, the flow valve is a duck bill valve. The flow valve can control a flow of the fluid mandrel such that the fluid mandrel flows in only a single direction. In some embodiments, the tubular member is a vein and the single direction is the same as a venous valve direction of the tubular member. The first and second plugs can be sealed to the tubular member using at least one of an adhesive, circumferential clamp, inflatable toroidal balloon or a suture.

In some embodiments, the fluid mandrel is comprised of a stagnant fluid. The fluid mandrel can be comprised of a flowing fluid. The fluid can flow is a single direction. In some embodiments, the fluid flows in a first direction and a second direction.

The system (and/or methods) can also include a pump to flow the flowing fluid. In some embodiments, the pump comprises a syringe, a hydrostatic head pump, or a displacement pump. The displacement pump can be a peristaltic pump, a piston pump or a diaphragm pump.

In some embodiments, the fluid forming the fluid mandrel is recirculated. In some embodiments, the fluid forming the fluid mandrel is not recirculated.

The fluid mandrel can have a lower voltage than the nozzle to create the electrical potential. The fluid mandrel can have a voltage of about −5 kV (e.g., −10 kV, −9 kV, −8 kV, −7 kV, −6 kV, −5 kV, −4.5 kV, −4 kV, −3.5 kV, −3 kV, −2.5 kV, −2 kV, −1.5 kV, −1 kV) and the nozzle can have a voltage of about +15 kV (e.g., 2.5 kV, 5 kV, 7.5 kV, 12 kV, 13.5 kV, 15 kV, 20 kV).

The tubular member can have a lower voltage than the nozzle to create the electrical potential. The tubular member can have a voltage of about −5 kV (e.g., −10 kV, −9 kV, −8 kV, −7 kV, −6 kV, −5 kV, −4.5 kV, −4 kV, −3.5 kV, −3 kV, −2.5 kV, −2 kV, −1.5 kV, −1 kV) and the nozzle can have a voltage of about +15 kV (e.g., 2.5 kV, 5 kV, 7.5 kV, 12 kV, 13.5 kV, 15 kV, 20 kV).

In some embodiments, the fluid source is charged. A power supply can be connected to at least one of the first and second plugs. Power can be transferred from the power supply to the fluid or tubular member by a metal wire. In some embodiments, two different fluids are used. The first fluid can be a non-conductive fluid configured to provide a supporting force to the tubular member, and the second fluid can be a conductive fluid used to deliver a charge to the external surface of the tubular member.

In some embodiments, the system also includes at least one motor in communication with at least one of the first or second plugs. The motor can be configured to rotate at least one of the first or second plugs. The at least one motor can be in direct communication with at least one of the first or second plugs. In some embodiments, the at least one motor is in indirect communication with at least one of the first or second plugs through at least one of a belt, a gear, or a wheel. The at least one motor can rotate either the first or the second plug. In some embodiments, the at least one motor rotates both the first and the second plug. A first motor can rotate the first plug and a second motor can rotate a second plug.

The system (and/or methods) can also include a weight or other force imposing mechanism connected to the second plug, for example, to control the magnitude of longitudinal tension applied to the tubular member. The at least one motor can be in communication with the first plug and the at least one motor can be configured to rotate the first plug.

In some embodiments, the system for electrospinning and the tubular member are in a horizontal configuration. The system for electrospinning and the tubular member can alternatively or additionally be in a vertical configuration.

At least one weight can be connected to at least one of the first or second plugs. The at least one weight can provide a tension force to the tubular member, for example, a predetermined and/or constant tension force. The at least one weight can comprise a fixed mass. The at least one weight can comprise a tensioning mechanism. A force transducer can be disposed on the at least one plug, weight or other system component in tension. The force transducer can be configured to detect a force applied to the tubular member by the at least one weight. The force can be a tensional force.

The system (and/or methods) can also include a synchronous drive system configured to rotate at least one of the first or second plugs. The synchronous drive system can prevent twisting of the tubular member. In some embodiments, the synchronous drive system is a timing belt system.

The fluid source can include a biologically compatible fluid, an electrically conductive fluid, and/or a dielectric fluid. The fluid source can comprise a first fluid and a second fluid. The first fluid can comprise a non-conductive fluid and the second fluid can comprise a conductive fluid. In some embodiments, the electrically conductive fluid is an electrolyte solution. The electrically conductive fluid can include saline, heparinized saline, ringers solution, and any combination thereof. The fluid source can include a phase change material. The phase change material can be a material selected from the group consisting of: a pluronic gel; an electro-rheological fluid; a non-Newtonian fluid characterized by changes in viscosity; and combinations of these. The phase change material can change phases based on one or more of: a temperature change, a pressure change, an electro-magnetic field; a level of shear rate applied or in response to a vibrational state; and combinations of these.

In some embodiments, the tubular member is a saphenous vein graft or other living tissue. The living tissue can include a vein, an artery, a lymphatic duct, a vas deferens, a tear duct, an intestine, an esophagus, a ureter, a urethra, a trachea, a bronchial conduit, a duct tissue, a Eustachian tube, a fallopian tube and any combination thereof. In some embodiments, the tubular member is an artificial tubular member. The artificial tubular member can include polytetrafluoroethylene; expanded polytetrafluoroethylene; polyester; polyvinylidene fluoride/hexafluoropropylene; silicone; polyethylene; polypropylene; polyester based polymer; thermoplastic rubber; polylactic acid/poly-L-lactide ("PLA/PLLA"), polyglycolic acid ("PGA"), polycaprolactone ("PCL"), and relative copolymers; collagen; elastin; glycosamminoglycans; proteoglycans; and any combination thereof.

In some embodiments, a pharmaceutical drug or other agent is included in the fluid source. Cells can be included in the fluid source.

In some embodiments, a pressure sensor is in communication with the fluid mandrel. The pressure sensor can be configured to measure a pressure the fluid mandrel exerts on the tubular member. A pressure control system can be in communication with the fluid mandrel. The pressure control system can be configured to monitor or control the pressure of the fluid mandrel. The pressure control system can control a geometry of the tubular member. The geometry controlled by the pressure control system can be an outer diameter of the tubular member. In some embodiments, the pressure control system can vary the geometry of the tubular member based on a location, such as a current location, of the at least one nozzle. The pressure control system can apply a tension or other force to the tubular member.

The at least one fiber can include a polymer. The polymer can be a natural polymer, a synthetic polymer and any combination thereof. The natural polymer can be a silk, chitosan, collagen, elastin, alginate, cellulose, polyalkanoate, hyaluronic acid, gelatin, and any combination thereof. The synthetic polymer can be a homopolymer, heteropolymer, co-polymer, block polymer, and any combination thereof.

The method (and/or systems) can also include flowing the fluid through the tubular member from a first end of the tubular member to a second end of the tubular member. The fluid can be recirculated from the second end of the tubular member to the first end of the tubular member. The fluid can oscillate in alternate directions within the tubular member. The fluid can be disposed at the second end of the tubular member.

A first plug can be inserted in a first end of the tubular member and a second plug can be inserted into a second end of the tubular member. The flow of the fluid mandrel can be controlled such that the fluid mandrel flows in only a single direction through the tubular member. The first and second plugs can be sealed to the tubular member. In some embodiments, the tubular member is rotated.

In some embodiments, a tensioning force is applied to the tubular member during electrospinning with a fluid mandrel. The tension force can help prevent kinking or distortion of the geometry and/or shape during rotation of the tubular member. In some embodiments, the geometry of the tubular member is controlled by controlling a pressure of the fluid mandrel exerted on an inside surface of the tubular member.

BRIEF DESCRIPTION OF THE DRAWINGS

The advantages of the systems and methods described herein, together with further advantages, may be better understood by referring to the following description taken in conjunction with the accompanying drawings. The drawings are not necessarily to scale, emphasis instead generally being placed upon illustrating the principles of the technology.

DESCRIPTION OF THE INVENTION

In general, electrospinning is a process that uses an electrical charge to draw a fiber, typically from a stream of solution comprised of a polymer dissolved in a solvent, dispensed through a source, for example a nozzle. The fibers that are produced from the electrospinning process are typically on the micro or nano scale. When a voltage is applied to a liquid meniscus facing the outlet of the nozzle and being replenished by an upstream flow, the liquid becomes charged. This charge causes electrostatic repulsion which counteracts the surface tension of the liquid. The liquid stream is attenuated and extruded and at a critical point. The stream dissociates into many other streams and is driven by the same electrostatic repulsion from a source such as a nozzle toward a target, for example, a substrate. Typically, streams dry significantly before the resulting fibers are deposited on a substrate. The electrospinning process can be used to electrospin a fiber matrix onto a tubular member.

Figure 1:
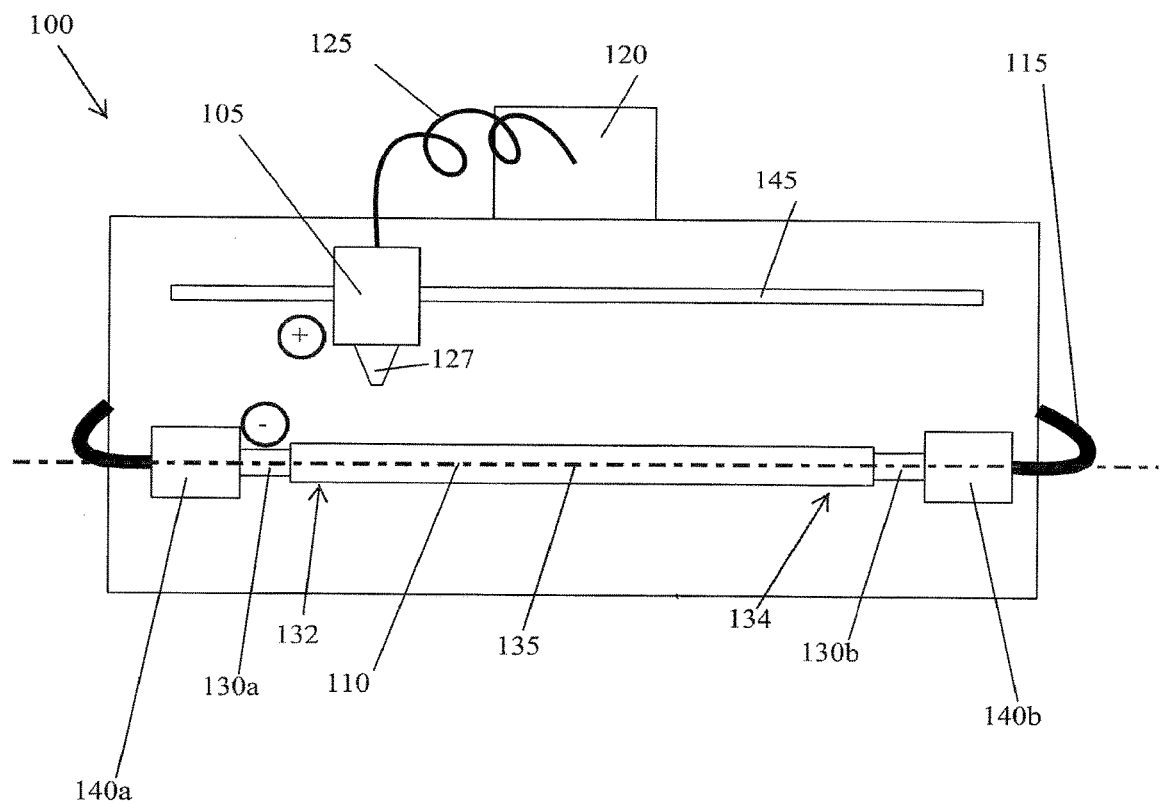
FIG. 1 is a schematic illustration of an example electrospinning system.

FIG. 1 shows an electrospinning system 100 that includes at least one nozzle 105, a tubular member 110, and a fluid source (not shown). The tubular member 110 is in a spaced relationship from the nozzle 105. For example, the tubular member 110 can be above or below the nozzle 105. In some embodiments, the tubular member 110 is located to the right or left of the nozzle 105. The distance between the tubular member 110 and the nozzle 105 can be, for example, about 5 cm to about 25 cm. Alternatively, multiple nozzles (not shown), for example nozzles of similar or dissimilar configurations, can be positioned in various orientations relative to the tubular member. Two or more of the multiple nozzles can deliver fibers to the tubular members simultaneously, or sequentially.

The fluid source can pressurize a lumen of the tubular member 110. To pressurize the lumen of the tubular member 110, fluid from the fluid source can be delivered to the tubular member by a delivery tube 115. When fluid from the fluid source is used to pressurize the lumen of the tubular member 110, the fluid forms a fluid mandrel within the tubular member 110. In some embodiments, fluid pressures range between about −30 mmHg and 100 mmHg, such as a fluid pressure of about 20 mmHg. In some embodiments, fluid pressures approximate values selected from the group consisting of: 5 mmHg, 10 mmHg, 15 mmHg, 20 mmHg, 25 mmHg, 30 mmHg, 35 mmHg, or 40 mmHg. Fluid from the fluid source can pressurize the lumen of the tubular member 110 with a varying pressure, such as a pressure that has a similar waveform to physiologic pressures, for example arterial pressure, or a waveform similar to but of lesser magnitude than an arterial pressure waveform. The pressure waveform can be between normal venous pressure and normal arterial pressure.

The fluid source can comprise a variety of different materials. For example, the fluid source can comprise heparinized saline. In some embodiments, the fluid source comprises a biologically compatible fluid, which is particularly important when the tubular member is a vein or other member harvested from a human or animal. This can avoid a subsequent cleaning or washing step. The fluid source can comprise an electrically conductive fluid, for example, an electrolyte solution. The electrically conductive fluid can comprise saline, heparinized saline, ringers solution, and any combination thereof. The fluid source can comprise a dielectric fluid. In some embodiments, two different fluids are used. A first fluid can be a non-conductive fluid configured to provide a supporting force to the tubular member 110, and the second fluid can be a conductive fluid used to deliver a charge to tubular member 110.

In some embodiments, the fluid source comprises a phase change material. The phase change material can be, for example, a pluronic gel, an electro-rheological fluid, or a non-Newtonian fluid characterized by changes in viscosity. The phase change material can change phases, for example, from a liquid to a solid or a gel, or from a gas to a liquid, based on temperature changes, pressure changes, or in response to an electro-magnetic field. A fluid source that can change phases in response to an external stimulus can allow an operator, nurse, or doctor to vary the pressure or shape of fluid mandrel along the tubular member by adjusting the external stimulus.

The tubular member 110 can be, for example, a saphenous vein graft or living tissue. The living tissue typically includes a vein, an artery, a lymphatic duct, a vas deferens, a tear duct, an intestine, an esophagus, a ureter, a urethra, a trachea, a bronchial conduit, a duct tissue, a Eustachian tube, a fallopian tube and any combination thereof. In some embodiments, the tubular member is an artificial tubular member. The artificial tubular member typically includes polytetrafluoroethylene, expanded polytetrafluoroethylene, polyester, polyvinylidene fluoride/hexafluoropropylene, silicone, polyethylene, polypropylene, polyester based polymer, thermoplastic rubber, and any combination thereof.

Pharmaceutical drugs or other agents can be included in a polymer solution that is used to electrospin a fiber matrix onto a tubular member 110. However, the electrospinning process can be harsh and can result in the degradation of the drug or agent. Therefore, in some embodiments, the pharmaceutical drug or other agent is included in the fluid source, which prevents the drugs or other agents from being placed in the harsh electrospinning environment. This configuration can allow the drug or other agent to be delivered directly to the tubular member or vein and can provide more efficient, targeted use of the drug or other agent. Examples of drugs that can be introduced include, without limitation, time release drugs, anti-clotting drugs (e.g., heparin, aspirin and clopidogrel), vasoactive drugs and molecules such as nitric oxide ("NO"), carbon monoxide ("CO"), papaverine, epinephrine and sodium nitroprusside, antibiotics, anti-proliferative agents, or analgesics (e.g. acetaminophen, naproxen, ibuprofen). In some embodiments, cells (from autogenous or allogeneic sources) such as endothelial cells, mesenchymal stem cells, endothelial progenitor cells, hematopoietic stem cells, bone marrow-derived progenitor cells, other adult stem cells, or embryonic stem cells are included in the fluid source. When the tubular member is a living tissue, cell treatment can help replenish the various cellular constituents of the tissue, or repair or remodel the tissue. The delivery of either stem cells, or fully differentiated adult cells via the fluid source, can provide biological support to the tubular member. Specifically, in the case of a saphenous vein graft, the delivered cells could be endothelial cells or endothelial progenitor cells that will populate the graft lumen in areas of native endothelial cell denudation. When the tubular member is a non-living tissue or material, inclusion of cells (e.g., cell seeding) can provide functionalization to the material such as antithrombogenicity.

An electrical potential can be applied between the nozzle 105 and one or both of the tubular member 110 and the fluid from the fluid source. The electrical potential can draw at least one fiber from the nozzle 105 to the tubular member 110. The tubular member 110 can act as the substrate for the electrospinning process, collecting the fibers that are drawn from the nozzle 105 by the electrical potential.

In some embodiments, the fluid mandrel and/or tubular member 110 has a lower voltage that the nozzle 105 to create the electrical potential. For example, the voltage of the fluid mandrel and/or tubular member 110 can be a negative or zero voltage while the voltage of the nozzle 105 can be a positive voltage. The fluid mandrel and/or tubular member 110 can have a voltage of about −5 kV (e.g., −10 kV, −9 kV, −8 kV, −7 kV, −6 kV, −5 kV, −4.5 kV-4 kV, −3.5 kV, −3.0 kV, −2.5 kV, −2 kV, −1.5 kV, −1 kV) and the nozzle 105 can have a voltage of about +15 kV (e.g., 2.5 kV, 5 kV, 7.5 kV, 12 kV, 13.5 kV, 15 kV, 20 kV). In some embodiments, the potential difference between the nozzle 105 and the fluid mandrel and/or tubular member 110 can be from about 5 kV to about 30 kV. This potential difference draws fibers from the nozzle 105 to the tubular member 110.

A polymer solution, stored in a polymer solution dispenser 120, can be delivered to the nozzle 105 through a polymer solution delivery tube 125. The electrical potential between the nozzle 105 and the tubular member 110 and/or the fluid can draw the polymer solution through the tip 127 of the nozzle 105. Electrostatic repulsion, caused by the fluid becoming charged from the electrical potential, counteracts the surface tension of a stream of the polymer solution at the tip 127 of the nozzle 105. After the stream of polymer solution is stretched to its critical point, one or more streams of polymer solution emerges from the tip 127 of the nozzle 105, and/or at a location below the nozzle 105, and move toward the negatively charged tubular member 110. Using a volatile solvent, the solution dries substantially during transit and the fiber is deposited on the tubular member 110.

The electrospinning system 100 can also include plugs 130a, 130b on each end of the tubular member 110. For example, a first plug 130a can be inserted at a first end 132 of the tubular member 110 and a second plug 130b can be inserted at a second end 134 of the tubular member 110. The first and second plugs 130a, 130b can rotate around axis 135. The rotation around axis 135 allows the fiber matrix to be deposited along all sides, or around the entire circumference, of the tubular member 110.

The first and second plugs 130a, 130b can be rotated by at least one motor 140a, 140b in direct or indirect communication with the first and/or second plugs 130a, 130b. In some embodiments, the electrospinning system includes a single motor that rotates one plug 130a, 130b at one end of the tubular member 110. In some embodiments, two motors 140a, 140b are used. For example, motor 140a can be in communication with plug 130a while motor 140b is in communication with 130b. The motors 140a, 140b can rotate the plugs 130a, 130b, and thus the tubular member 110, at the same rate or at different rates. The rate of rotation of the plugs 130a, 130b and tubular member 110 can depend on how the fiber matrix needs to be applied to the tubular member 110. For example, for a thicker fiber matrix, the rotation rate can be slower than if a thinner fiber matrix is desired.

In addition to the tubular member 110 rotating around axis 135, the nozzle 105 can move along a drive assembly 145. Additionally or alternatively, nozzle 105 can be constructed and arranged to rotate around axis 135. The length of the drive assembly 145 can vary based on the length of the tubular member 110 to which a fiber matrix will be applied. For example, the length of the drive assembly 145 can be about 10 cm to about 50 cm. The nozzle 105 can move along the drive assembly 145 to apply a fiber matrix to the entire length, or specific portions of a length, of a tubular member 110. For example, the nozzle 105 can be controlled such that specific portions along the length of the tubular member 110 are reinforced with a greater amount of fiber matrix as compared to other or remaining portions. In addition, the tubular member 110 can be rotating around axis 135 while the nozzle 105 is moving along the drive assembly 145 to provide control over the location on the tubular member 110 where the fiber matrix is applied.

The first and second plugs 130a, 130b can be sealed to the tubular member 110 by using at least one of an adhesive, a circumferential clamp, inflatable toroidal balloon, or a suture. Sealing the plugs 130a, 130b can decrease and/or eliminate the amount of fluid within the fluid mandrel that exits the electrospinning system 100 around the area where the plugs 130a, 130b meet the tubular member 110. In some embodiments, the plugs 130a, 130b are sealed to the tubular member 110 by a friction fit.

The first and second plugs 130a, 130b can be disposable. Disposable plugs can be inexpensive to manufacture and can also ensure that the plugs are sterile and otherwise sanitary before use. This is particularly important where the tubular member 110 is within the human body. In addition, disposable plugs can eliminate the need for operators or nurses to clean and disinfect plugs after use.

The system 100 can also include a power supply (not shown). The power supply can be connected, either directly or indirectly, to at least one of the first and second plugs 130a, 130b. Power can be transferred from the power supply to the fluid and/or tubular member 110 by, for example, a wire. The power supplied to the fluid and/or tubular member 110 can provide the potential difference between the nozzle 105 and the tubular member 110.

In some embodiments, a first portion of an electrospun fiber matrix is applied to the tubular member 110. A pressure can be applied to the inside of tubular member 110 to elongate the tubular member 110 to a desired pressurized length. Tubular member 110 can be secured (e.g. by repositioning one or more of plugs 130a and 130b) at a length different than its starting length, and another portion of the electrospun fiber matrix can be applied to the tubular member 110.

In some embodiments, a pressure is applied to the inside of tubular member 110, and tubular member 110 is allowed to elongate. Subsequently, the tubular member 110 can be secured at a length different than its starting length (e.g. by repositioning one or more of plugs 130a and 130b). Pressure can be reduced within the tubular member 110 to allow for a reduction in the diameter of the tubular member 110 while approximately maintaining the pressurized length. A fiber matrix can be applied around the tubular member 110.

The pressure applied to the inside of tubular member 110 can be approximately the same as arterial pressure, such as the patient's arterial pressure. In some embodiments, the pressure applied to the inside of tubular member 110 is approximately the same as venous pressure, such as the patient's venous pressure. The pressure applied to the inside of tubular member 110 can be lower than arterial pressure. In some embodiments, the luminal pressure applied within tubular member 110 is negative relative to the outside of the tubular member 110.

Figure 2:
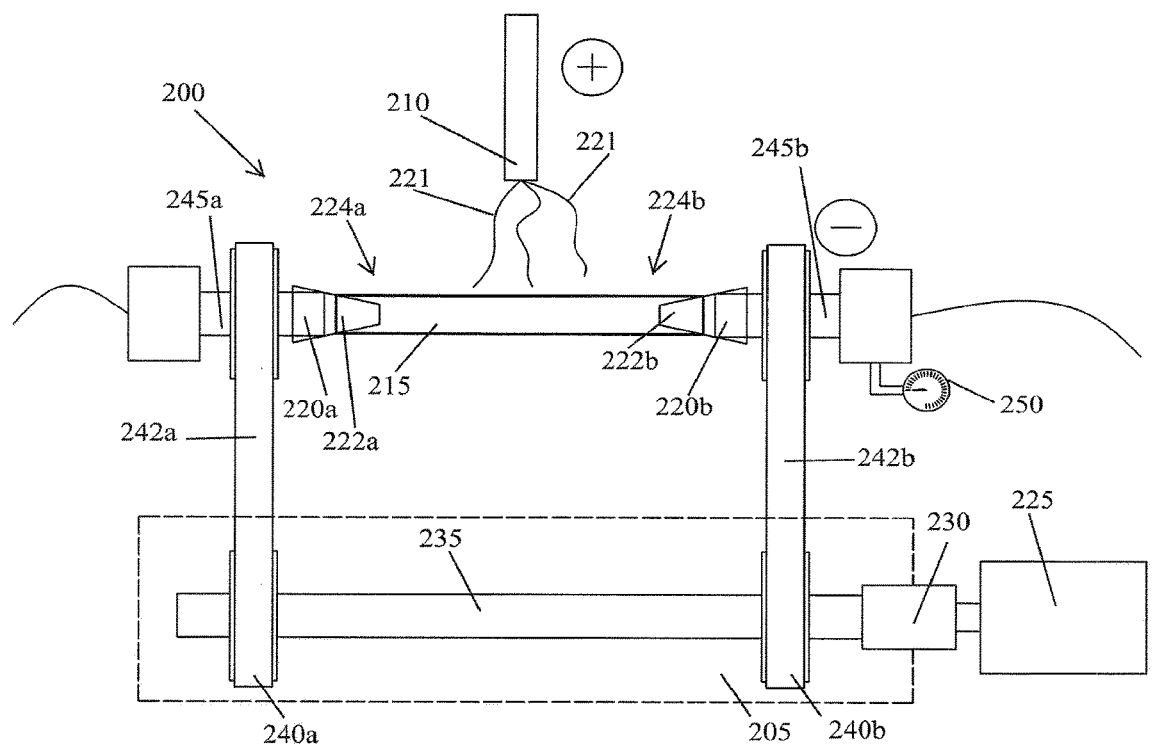
FIG. 2 is a schematic illustration of an example electrospinning system including a synchronous drive system.

FIG. 2 shows an electrospinning system 200, including a synchronous drive system 205. The electrospinning system includes at least one nozzle 210, a tubular member 215, and a fluid source (not shown). In addition, two plugs 220a, 220b are located at the ends of the tubular member 215.

FIG. 2 also shows fibers 221 emerging from the nozzle 210 and going toward the tubular member 215. The at least one fiber 221 can be, for example, a polymer. The polymer can be a natural polymer, a synthetic polymer, and a combination thereof. The natural polymer can be a silk, chitosan, collagen, elastin, alginate, cellulose, polyalkanoate, hyaluronic acid, gelatin, or any combination thereof. The synthetic polymer can be a homopolymer, heteropolymer, co-polymer, block polymer, and any combination thereof.

Either the first or second plug 220a, 220b can include a flow valve 222a, 222b, respectively. The flow valve 222a, 222b can be, for example, a duck bill valve. The flow valve 222a, 222b can control a flow of the fluid mandrel such that the fluid mandrel flows in only one direction. Alternatively or additionally, the flow valve 221a and/or 222b can be configured to retain pressure within the tubular member 215. For example, the flow of the fluid mandrel can be from a first end 224a of the tubular member 215 to a second end 224b of the tubular member 215, or vice versa. In some embodiments, the tubular member 215 is a vein, and the fluid flows in a single direction that is the same as a venous valve direction of the tubular member 215 (i.e. the same direction as the flow of blood through the vein prior to harvesting). This flow path can ensure that the vein is not damaged by the fluid mandrel flowing in a direction opposite to the normal flow of fluid within the vein. In some embodiments, the fluid can flow in a first direction and a second direction.

The fluid mandrel can be comprised of a stagnant fluid or a flowing fluid. When the fluid mandrel is comprised of a stagnant fluid, the fluid enters the tubular member 215 either from the first end 224a or the second end 224b or both. If the tubular member 215 is a vein, then the fluid can enter the vein in the same direction as the venous valve direction. After the fluid enters the tubular member 215 and the desired pressure is reached (e.g., sufficient pressure to prevent undesired undulation of the tubular member 215 during the electrospinning process), the ends of the tubular member 215 can be sealed so that fluid can no longer enter or leave the tubular member 215. The electrospinning process then occurs with the fluid in the tubular member 215 being stagnant, for example, with no fluid entering or leaving the tubular member 215 after the ends of the tubular member 215 are sealed.

When the fluid in the tubular member 215 is flowing, a pump (not shown) can be used to flow the flowing fluid. The pump can comprise, for example, a syringe, a hydrostatic head pump, or a displacement pump. The displacement pump can be, for example, a peristaltic pump, a piston pump or a diaphragm pump. The pump can provide a continuous single direction fluid flow, or a fluid flow that changes direction and/or oscillates from one direction to the other.

The fluid in the tubular member 215 can be recirculated when the fluid is flowing. In some embodiments, the fluid forming the fluid mandrel is not recirculated, and instead fresh fluid is provided from the fluid source or, for example, one or more reservoirs.

The electrospinning system 200 can also include at least one motor 225 in indirect communication with at least one of the first or second plugs 220a, 220b. The indirect communication can occur, for example, through at least one of a belt, a gear, a wheel, or a pulley system. For example, synchronous drive system 205 includes a shaft coupler 230 that couples the motor 225 to a shaft 235, and two timing pulleys 240a, 240b. The two timing pulleys 240a, 240b have a timing belt 242a, 242b, respectively. The timing pulleys 240a, 240b can be connected to tees 245a, 245b, which are in turn are connected to plugs 220a, 220b, respectively.

The synchronous drive system 205 can indirectly rotate the tubular member 215. For example, the motor 225 is coupled to the shaft 235 by coupler 230. The motor 225 can rotate the shaft 235 in either a clockwise or counter clockwise direction. The shaft 235 in turn rotates the timing pulleys 240a, 240b and timing belts 242a, 242b. The timing pulleys 240a, 240b and timing belts 242a, 242b rotate the tees 245a, 245b, which rotates the tubular member 215.

Alternatively, the synchronous drive system 205 can be configured to rotate the first and second plugs 220a, 220b independently, for example by two independent motors (not shown). The synchronous drive system 205 can prevent twisting of the tubular member 215 by controlling the rates at which each of the first and second plugs 220a, 220b rotate.

In some embodiments, the electrospinning system 200 also includes a pressure control system or a pressure sensor 250 that is in communication with the fluid mandrel. The pressure sensor 250 is configured to measure a pressure the fluid mandrel exerts on the tubular member 215. The pressure sensor 250 can be used to control the pressure exerted on the lumen of the tubular member 215.

Figure 3A:
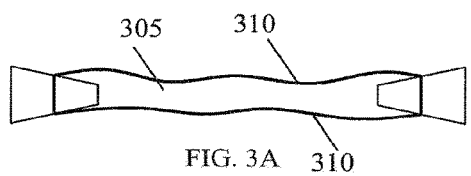
FIG. 3A is a schematic illustration of an example tubular member without an applied pressure.
Figure 3B:
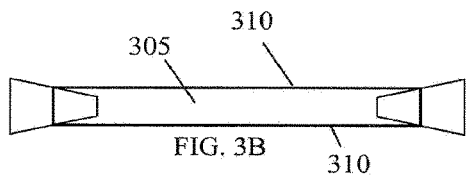
FIG. 3B is a schematic illustration of an example tubular member with an applied pressure.

The pressure control system or pressure sensor 250 can be used to control the topography or other geometric parameter of the tubular member 215. For example, FIG. 3A shows a tubular member 305 without an applied pressure and FIG. 3B shows the tubular member 305 with an applied pressure. Referring to FIG. 3A, the tubular member 305 is not under pressure. The walls 310 of the tubular member 305 are not straight and have various sized and shaped curves. Applying a fiber matrix to the tubular member 305 of FIG. 3A can be difficult due to these curves and/or the application can result to an unacceptable fluid path for the fluid mandrel. To better apply a fiber matrix to the tubular member 305, the lumen of the tubular member 305 can be pressurized with a fluid mandrel. Referring to FIG. 3B, the tubular member 305 is under pressure. The pressure can cause the walls 310 to become generally straight. As shown in FIGS. 3A and 3B, the pressure control system can control the cross-sectional geometry of the tubular member 305. The force applied by the pressure control system can be a tension force that causes the walls 310 of the tubular member 305 to go from being slack or curvy, as shown in FIG. 3A, to tight, straight, or continuously curved as shown in FIG. 3B.

In some embodiments, the pressure control system can vary the geometry of the tubular member 310 based on a location of the at least one nozzle (not shown). In some embodiments, the pressure is increased when the nozzle is delivering fibers to one portion of tubular member 305, and the pressure is decreased when the nozzle is delivering fibers to a different portion of tubular member 305. Pressure increases can coincide with tubular member 305 portions that are of insufficient diameter or contain one or more folds. Pressure decreases can coincide with tubular member portions that are of sufficient diameter or a diameter that is desired to be reduced. One or more magnetic, resistive or other position sensors (not shown) can be included to coordinate nozzle position relative to the tubular member 305. The fluid pressure can be controlled to achieve pressure-mediated inflation and/or deflation of the tubular member 305, such as to customize a size of the tubular member 305.

Figure 4A:
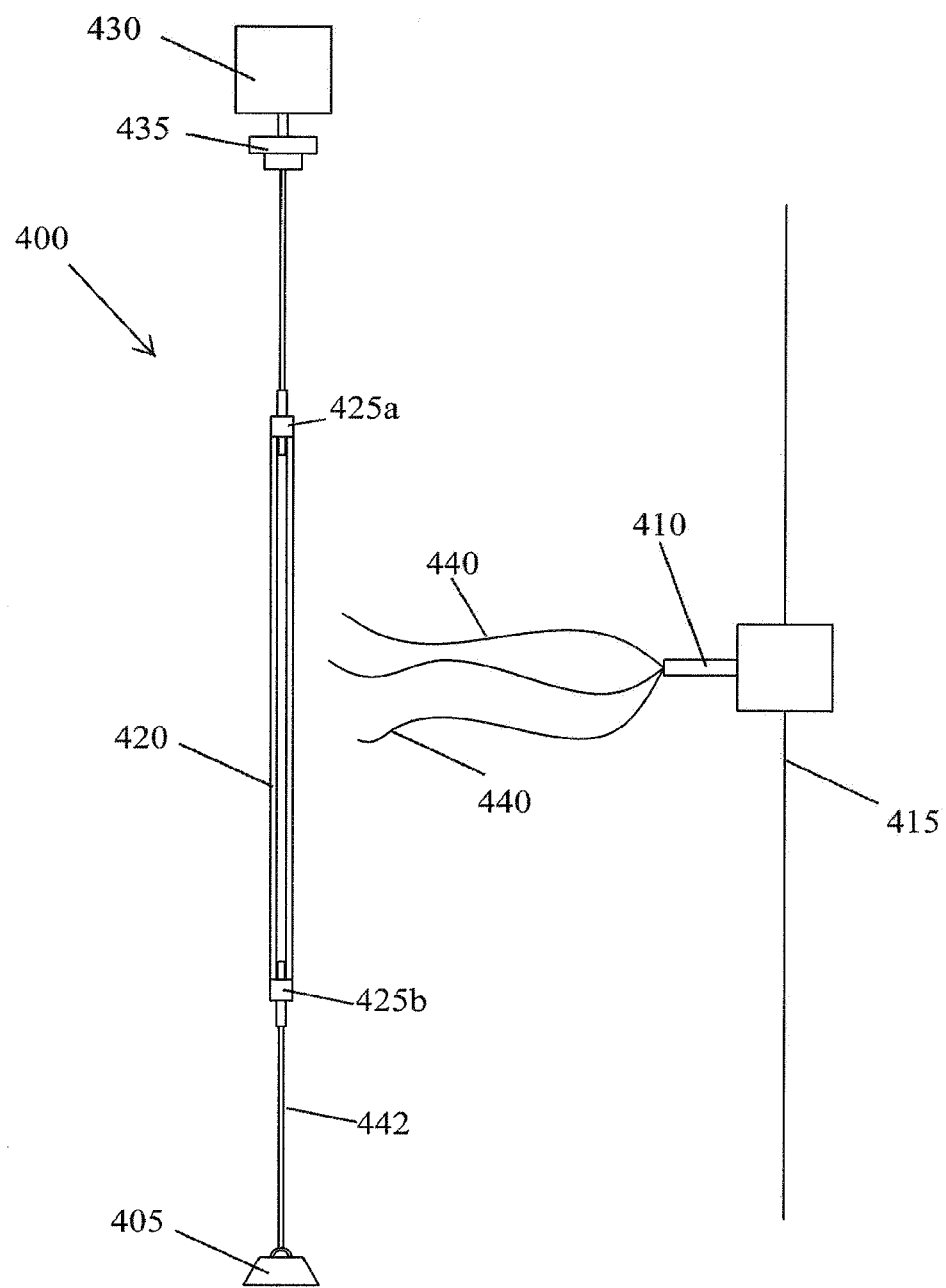
FIG. 4A is a schematic illustration of an example electrospinning system including a tensioning weight configured for a vertical position.
Figure 4B:
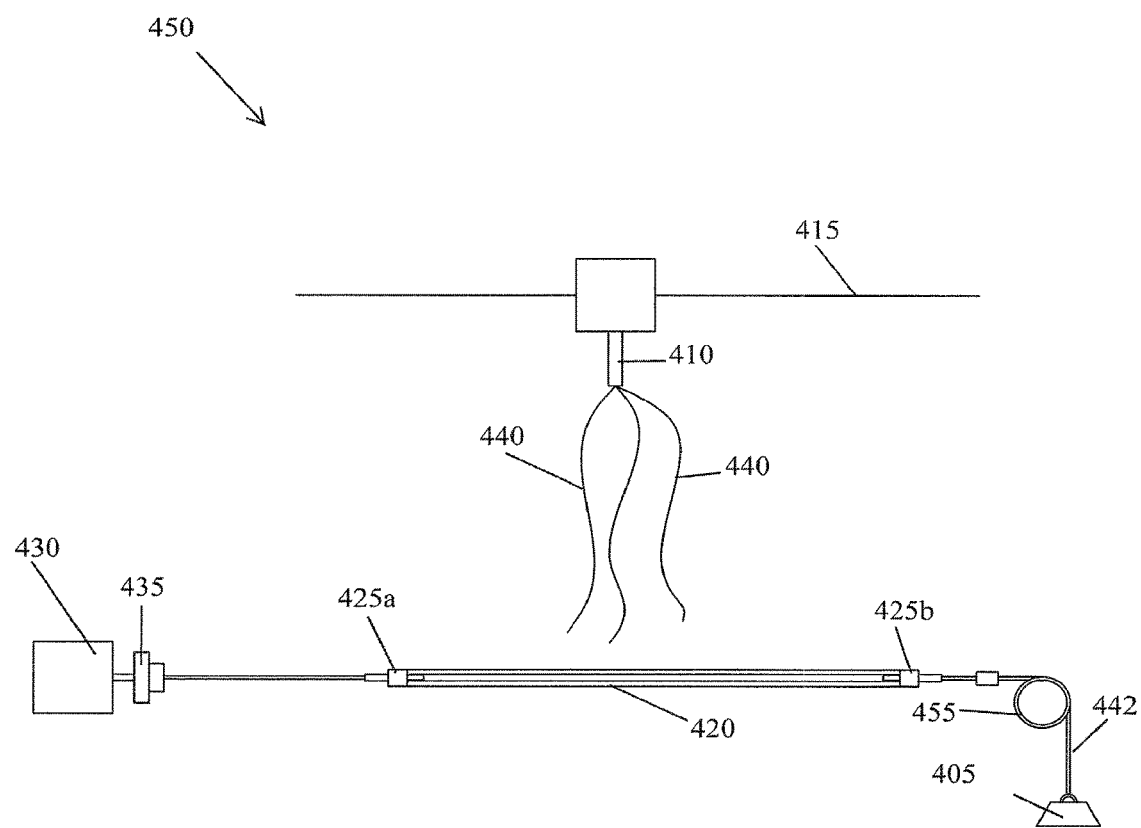
FIG. 4B is a schematic illustration of an example electrospinning system including a tensioning weight configured for a horizontal position.

The electrospinning system can be in a vertical or horizontal position. FIG. 4A shows an electrospinning system 400 including a tensioning weight 405 configured for a vertical position. FIG. 4B shows an electrospinning system 450 including a tensioning weight 405 configured for a horizontal position. FIGS. 4A and 4B both include at least one nozzle 410, a drive assembly 415 on which the nozzle 410 can move, a tubular member 420, plugs 425a, 425b, a motor 430, a coupler 435 between the motor and plugs 425a, 425b, and at least one fiber 440 between the nozzle 410 and the tubular member 420. The weight 405 is connected to plug 425b or the tubular member by a wire assembly 442.

The weight 405 can be connected to at least one of the plugs 425a, 425b. As shown in FIGS. 4A and 4B, a single motor 430 can be used to rotate the tubular member 420. The weight 405 provides a tension force to the tubular member 420. The tension force can be adjusted by adjusting the mass of the weight 405. For example, a heavier mass can provide a greater tension force and a lighter mass can provide less tension force.

In both the vertical and horizontal positions, gravity can be used to apply the tension. As shown in FIG. 4A, when the electrospinning system 400 is in a vertical position, the weight 405 can be suspended from the system. The force applied to the tubular member 420 will be approximately equal to the mass of the weight 405 times gravity. As shown in FIG. 4B, when the electrospinning system 450 is in a horizontal configuration, the weight 405 can still be used to apply tension to the tubular member 420. A pulley 455 can be used to translate the vertical force to a horizontal force applied to the tubular member 420.

In some embodiments, a force transducer (not shown), for example a strain gauge or load cell, is positioned on or near one or more components of system 400 to measure the tension force in wire assembly 442 and/or tubular member 420. The force transducer can be configured to detect and/or measure a force applied to the tubular member by or at the weight 405. The force can then be adjusted by adjusting the mass of the weight 405. In some embodiments, the weight 405 comprises a fixed mass. Force adjustments can be used to change the geometry of tubular member 420 during the electrospinning process to, for example, straighten a portion of the tubular member 420 and/or remove one or more folds present in the wall of the tubular member 420. Alternatively, one or more stretching or tensioning mechanisms can be used in addition or as an alternative to weight 405.

Figure 5:
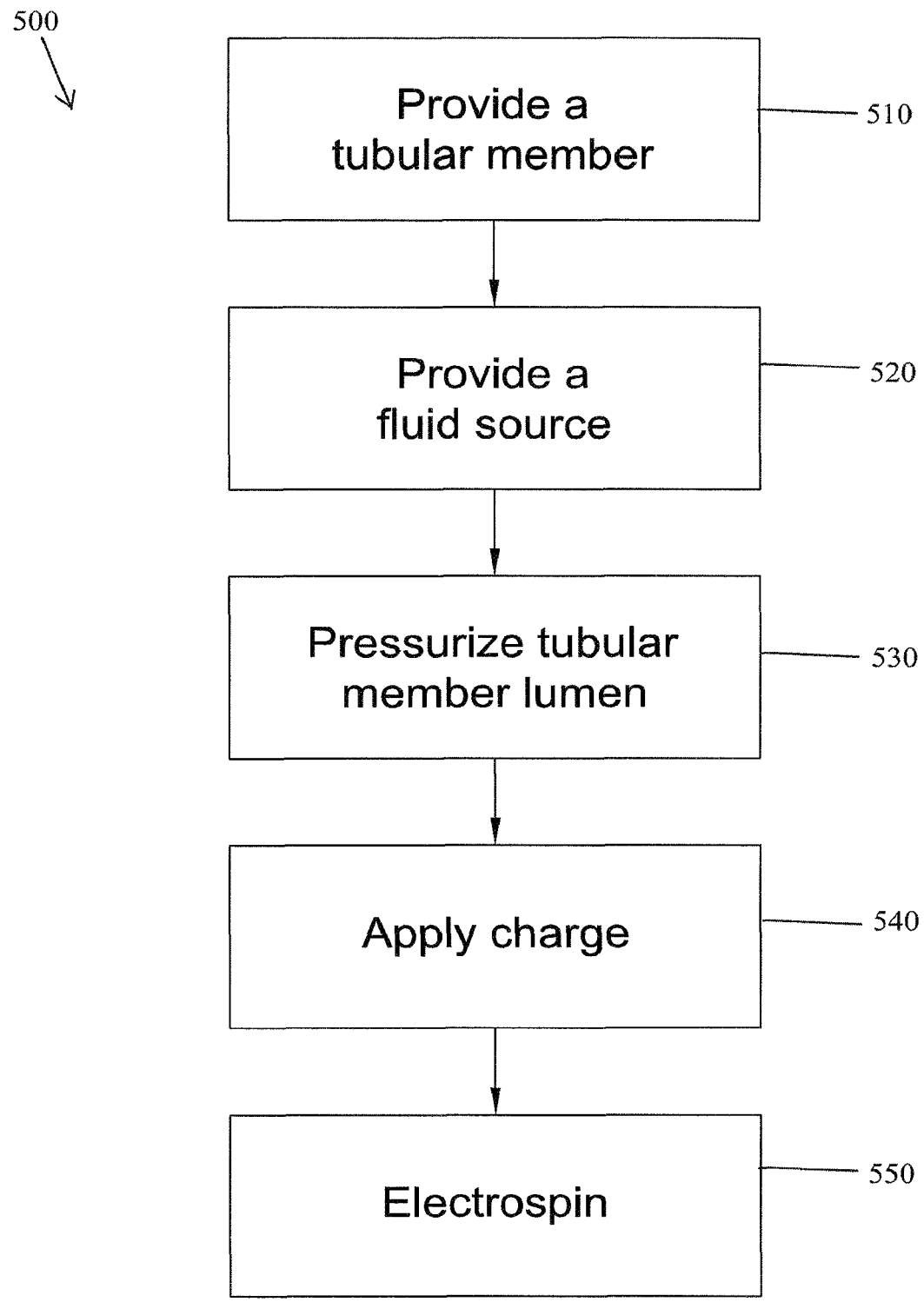
FIG. 5 is a flow chart of an example method for depositing a fiber matrix on a tubular member.

FIG. 5 is a flow chart 500 of a method for depositing a fiber matrix on a tubular member. A tubular member and a fluid source are provided (steps 510, 520, respectively). A lumen of the tubular member is pressurized with fluid from the fluid source (step 530). The tubular member and/or the fluid are charged (step 540). A fiber matrix is electrospun onto the tubular member (step 550).

In some embodiments, the method also includes flowing the fluid through the tubular member from a first end of the tubular member to a second end of the tubular member. The fluid can be recirculated from the second end of the tubular member to the first end of the tubular member. In some embodiments the fluid is not recirculated and instead the fluid is disposed of when it reaches the second end of the tubular member.

A first plug can be inserted into the first end of the tubular member and a second plug can be inserted into the second end of the tubular member. The flow of the fluid can be controlled such that the fluid flows in only a single direction through the tubular member, for example, from the first end to the second end. In some embodiments, at least one of the first or second plugs is sealed to the tubular member. The tubular member can be rotated to provide an even distribution of the fiber matrix around the tubular member. A tensioning force can be applied to the tubular member, for example, by using a weight to modify the geometry of the tubular member. The geometry of the tubular member can also be controlled by controlling, for example, the pressure of the fluid that is exerted on an inside surface of the tubular member.

A pharmaceutical drug or other agent can be provided to the fluid source to provide, for example, localized drug treatment. In addition, cells can be provided to the fluid source. Drugs and other agents, as well as cells, can be absorbed by the tubular member prior to, during, or after the electrospinning process.

One skilled in the art will realize the systems and methods described herein can be embodied in other specific forms without departing from the spirit or essential characteristics thereof. The foregoing embodiments are, therefore, to be considered in all respects illustrative rather than limiting of the invention described herein. Scope of the claimed systems and methods is thus indicated by the appended claims, rather than by the foregoing description, and all changes that come within the meaning and range of equivalency of the claims are, therefore, intended to be embraced therein.

What is claimed is:

1. A system for electrospinning a fiber matrix onto a tubular member to form a vascular graft device, the system comprising:
   at least one nozzle;
   a tubular member in a spaced relationship to the at least one nozzle, the tubular member defining an internal lumen;
   a fluid source that pressurizes the internal lumen of the tubular member with a fluid; and
   a pressure control system operatively connected to the fluid source and configured to control a pressure exerted on the internal lumen of the tubular member by the fluid source;
   wherein an electrical potential is applied between the at least one nozzle and the tubular member and/or the fluid within the internal lumen of the tubular member, the electrical potential drawing at least one fiber from the at least one nozzle to the tubular member, and wherein the system does not comprise a mechanical type of mandrel inserted through the lumen of the tubular member.

2. The system of claim 1, wherein the fluid source is configured to pressurize the internal lumen of the tubular member with a varying pressure.

3. The system of claim 1, wherein the fluid source is configured to pressurize the internal lumen with a stagnant fluid.

4. The system of claim 1, wherein the fluid source is configured to pressurize the internal lumen with a flowing fluid.

5. The system of claim 4, wherein the fluid source is configured to pressurize the internal lumen with the flowing fluid that is recirculated.

6. The system of claim 1, wherein the fluid that pressurizes the internal lumen has a voltage lower than a voltage of the at least one nozzle.

7. The system of claim 6, wherein the fluid that pressurizes the internal lumen has a voltage of about −5 kilovolts (kV) and the at least one nozzle has a voltage of about +15 kV.

8. The system of claim 1, wherein the fluid source is configured to pressurize the internal lumen with the fluid that comprises heparinized saline.

9. The system of claim 1, wherein the fluid source is configured to pressurize the internal lumen with the fluid that is selected from the group consisting of: an electrically conductive fluid; a dielectric fluid; and a combination thereof.

10. The system of claim 1, wherein the fluid source is configured to pressurize the internal lumen with the fluid that comprises a phase change material.

11. The system of claim 1, further comprising a pressure sensor in communication with the fluid, the pressure sensor configured to measure a pressure the fluid exerts on the tubular member.

12. The system of claim 11, wherein the pressure sensor controls a topography of the tubular member.

13. The system of claim 1, wherein the fluid source is configured to pressurize the internal lumen of the tubular member to a pressure that does not exceed about 40 mmHg.

14. The system of claim 1, wherein the tubular member is a living tissue.

15. The system of claim 14, wherein the tubular member comprises a saphenous vein graft.

16. The system of claim 14, wherein the tubular member comprises a harvested vein segment.

* * * * *